United States Patent [19]

Banuchi

[11] Patent Number: 5,584,851
[45] Date of Patent: Dec. 17, 1996

[54] HAIR TRANSPLANT INSTRUMENT AND METHOD FOR TRANSPLANTING HAIR GRAFTS

[76] Inventor: Isabel M. Banuchi, Avendida Domenech 302, Hato Rey, Puerto Rico, 00918

[21] Appl. No.: 438,201

[22] Filed: May 9, 1995

[51] Int. Cl.⁶ ................................. A61B 17/34
[52] U.S. Cl. .................. 606/187; 606/132; 606/191; 623/15
[58] Field of Search .................. 606/187, 133, 606/1, 191, 132; 623/15

[56] References Cited

U.S. PATENT DOCUMENTS

| | | | |
|---|---|---|---|
| 3,522,809 | 8/1970 | Cornell | 128/305 |
| 3,561,449 | 2/1971 | Bellantoni | 128/305 |
| 3,699,969 | 10/1972 | Allen | 128/330 |
| 3,867,942 | 2/1975 | Bellantoni | 128/305 |
| 3,998,230 | 12/1976 | Miller | 606/187 |
| 4,122,855 | 10/1978 | Tezel | 128/310 |
| 4,244,370 | 1/1981 | Furlow et al. | 606/187 |
| 4,423,837 | 1/1984 | Clements . | |
| 4,476,864 | 10/1984 | Tezel | 128/305 |
| 5,269,801 | 12/1993 | Shiau | 606/187 |

FOREIGN PATENT DOCUMENTS

| | | | |
|---|---|---|---|
| 2666978A | 3/1992 | France | 606/187 |
| 2809327 | 4/1979 | Germany | 606/187 |

*Primary Examiner*—Robert A. Hafer
*Assistant Examiner*—Justine Yu
*Attorney, Agent, or Firm*—Parkhurst, Wendel & Burr, L.L.P.

[57] ABSTRACT

An instrument for transplanting a plurality of hair grafts into respective pre-formed holes in the skin of a patient, includes an elongate hollow tube having first and second ends, and an open channel extending along a length of the tube, the tube being adapted to hold a plurality of hair grafts, and a dilation device for dilating the pre-formed holes in the skin of the patient, including a spoon-shaped tip extending from the first end of the tube. Additionally, a method for transplanting hair grafts is provided, wherein the tube is loaded with a plurality of hair grafts, and the spoon-shaped tip is successively inserted into the pre-formed holes to dilate same, and sliding the hair grafts into respective, dilated pre-formed holes. In another aspect of the invention, the hair transplant instrument has a multiplicity of channels, each containing a hair graft.

3 Claims, 2 Drawing Sheets

FIG. 1
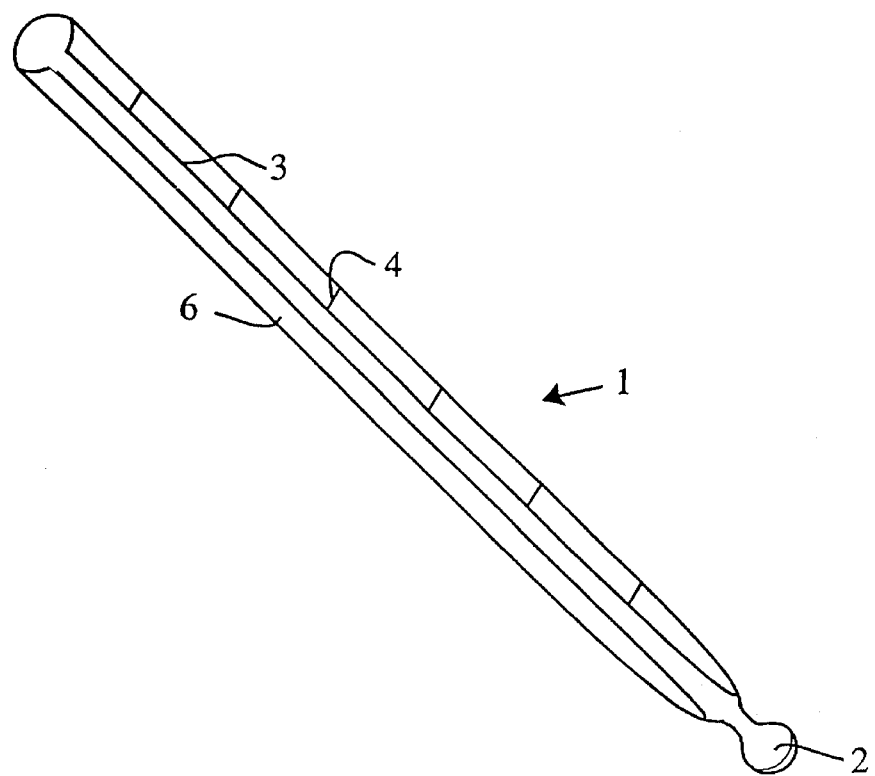
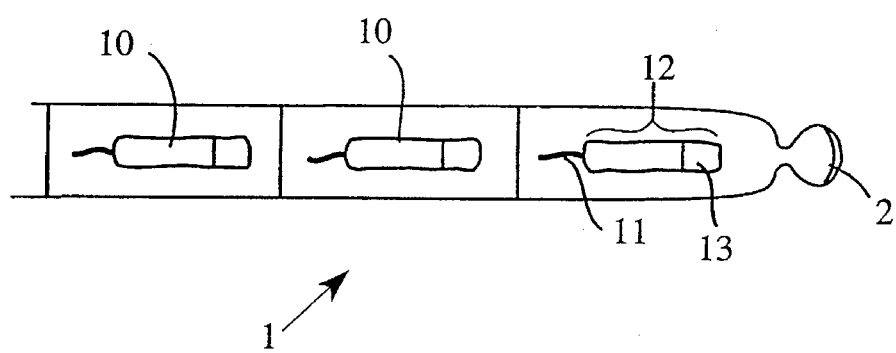
FIG. 2

HAIR TRANSPLANT INSTRUMENT AND METHOD FOR TRANSPLANTING HAIR GRAFTS

BACKGROUND OF THE INVENTION

The present invention relates to an instrument and method for transplanting hair, particularly for transplanting hair in the scalp of a bald patient.

One of the most difficult aspects of transplanting hair is that the operation is tedious and time consuming. More particularly, a doctor carrying out a hair transplant procedure must repetitively retrieve grafts and individually place those grafts in preformed holes in the scalp of the patient. Since the number of grafts during an individual procedure typically ranges from hundreds to thousands, repetitively locating successive empty holes in the scalp can be exhausting for the doctor.

DISCUSSION OF THE PRIOR ART

U.S. Pat. No. 5,269,801 to Shiau discloses an instrument for carrying out hair transplants. The '801 patent discloses a device for implanting hair-containing grafts, including a guiding tube for receiving a single graft and a pushing stick inserted through one end of the guiding tube. The guiding tube is formed of a rolled plastic sheet such that the longitudinal edges overlap each other, and one end of the tube forms an inclined surface which is adapted to be inserted into a slit hole formed in the scalp of a patient. Only one graft is provided in the tube at a time and the graft is forced into the incision (slit hole) via the pushing stick. Downward movement of the pushing stick enlarges the incision due to slight outward expansion of the guiding tube.

In the '801 patent, although, apparently, forceps are not used to prevent damage of the grafts, the procedure is a time-consuming one, since only a single graft is provided in the guiding tube at a time, thus requiring repetitive reloading of the tube.

The present invention has been developed to overcome the deficiencies of the prior art instruments and methods described above. Specifically, the present invention provides an instrument and a method of using same that permits successive placements of grafts in pre-formed holes in the skin of a patient without high repetition of reloading of the instrument, or requiring successive retrieval of grafts. The present invention aims to reduce greatly the implantation time during the hair transplant procedure.

SUMMARY OF THE INVENTION

To meet the objects of the present invention, the present invention provides a hair transplant instrument including an elongate hollow tube having first and second ends, and an open channel extending along a length of the tube, the tube being adapted to hold a plurality of hair grafts, and dilation means for dilating the pre-formed holes in the skin of a patient, the dilation means comprising a spoon-shaped tip extending from the first end of the tube. Additionally, a method for transplanting hair grafts is provided, using the above-described instrument, and includes the steps of loading the instrument with a plurality of hair grafts such that the bulbs thereof extend toward the first end of the tube, successively inserting the spoon-shaped tip into pre-formed holes in the skin of a patient to dilate the holes, and successively sliding the hair grafts through the tube, along the spoon-shaped tip, and into respective pre-formed holes, such that the bulbs of the hair grafts are placed in the respective pre-formed holes.

BRIEF DESCRIPTION OF THE DRAWINGS

FIG. 1 is a perspective view of the hair transplant instrument aspect of the present invention;

FIG. 2 is a cross-sectional view of the hair transplant instrument of the present invention, showing a plurality of grafts therein;

DETAILED DESCRIPTION OF THE PREFERRED EMBODIMENTS

Figure 3:
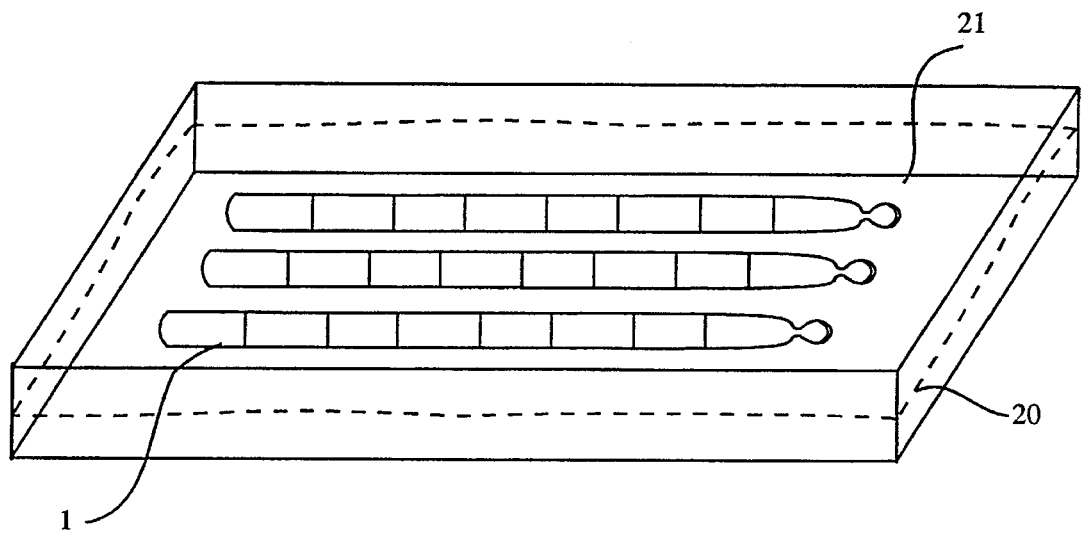
FIG. 3 provides a perspective view of a kit of the hair transplant instruments of the present invention, which may be provided to carry out a hair transplant procedure.

As shown in FIGS. 1 and 2, the present invention provides a hair transplant instrument 1 that includes an elongate hollow tube 6. Extending from a first end of the tube 6, a spoon-shaped tip 2 is provided, while a second, opposite end of the tube 6 is open. Additionally, an open channel 3 is formed to extend along the length of the tube to receive hair grafts and bias grafts with forceps 6. Preferably, tube 6 is formed of a clear plastic material, such that it is disposable. A plurality of indicia marks 4 are spaced apart along the tube 6.

Advantageously, the hair transplant instrument is between about 1 mm and about 5 mm in diameter, and about 5 inches in length. The spoon-shaped tip is preferably 1–2 mm in width, depending on the size of the pre-formed slits or holes in the skin or scalp of a patient. Additionally, the spoon-shaped tip may have a slightly curved or concave contour, to aid in positioning of the grafts.

FIG. 2 shows placement of grafts 10 in tube 6. As shown, the grafts 10 are positioned between the indicia marks 4, and are oriented such that bulb 12 having fatty portion 13 extends toward the first end of the tube, from which the spoon-shaped tip extends, and that hair 11 extends toward the second, opposite end of the tube 6.

To carry out the hair transplant procedure, the instrument 1 is first loaded with grafts as shown in FIG. 2, and is held over the area of skin of the patient containing pre-formed holes, each of which is intended to receive a graft. The instrument is generally held in a perpendicular slightly inclined manner with respect to the treated skin scalp area of the patient. Then, the instrument is advanced so as to fit the spoon-shaped tip into a pre-formed hole (slit), to dilate (i.e., expand) the hole. Subsequently, a first graft is urged through the first end of the tube and along the spoon-shaped tip such that the hair shaft and bulb 12 of the graft 10 is placed within the pre-formed hole. Advantageously, the grafts may be biased into the pre-formed hole with forceps, such as jeweler's forceps. The above-described operation is repetitively carried out with respect to a number of pre-formed holes, corresponding to the number of grafts contained in the preloaded instruments. Subsequent grafts are moved downward to the first end of the tube to be ready for placement in respective pre-formed holes by inserting the forceps through the open channel and biasing very gently the graft downward toward the first end.

Figure 4:
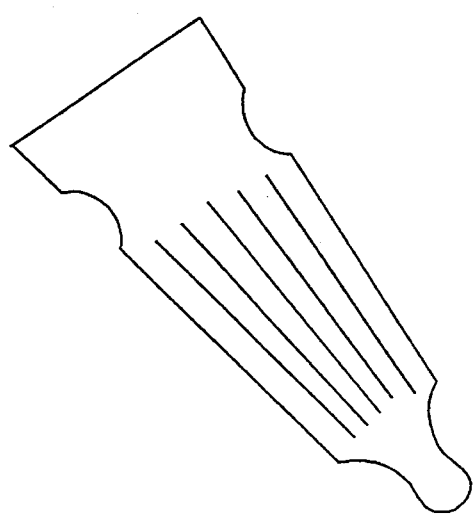
FIG. 4 shows another embodiment of the invention which is a funnel device containing a plurality of hair shafts and bulbs and the spoon-shaped tip of the hair transplant instrument of this invention.

The inventor has found that by using the instrument and method of the present invention the time required to carry out an entire transplant may be reduced by a factor of one-half. Additionally, the instrument is very simple, and a plurality of those instruments may be loaded with grafts prior to start of the operation. The unloaded instruments may be reloaded with grafts by an assistant, thus requiring as many instruments as necessary. As shown in FIG. 3, instruments 1 are provided in container 20 filled with saline 21 to form a kit. As shown in FIG. 4, the hair transplant instrument of the present invention can be a funnel containing a plurality of grafts containing a hair shaft and bulb and having a spoon-shaped tip.

What is claimed is:

1. A method for transplanting hair grafts each having a bulb and hair extending therefrom, comprising the steps of:

loading an instrument with a plurality of hair grafts such that said instrument simultaneously holds said plurality of hair grafts, said instrument including (i) a hollow tube for receiving the hair grafts, said tube having first and second ends, and (ii) a spoon-shaped tip extending from the first end of the tube, said instrument being loaded such that the bulbs of the hair grafts extend toward the first end of the tube;

successively inserting the spoon-shaped tip into pre-formed holes in the skin of a patient to dilate the pre-formed holes; and successively sliding each of the hair grafts through said tube, along said spoon-shaped tip, and into a respective pre-formed hole, such that the bulbs of hair grafts are placed in respective pre-formed holes.

2. The method of claim 1, wherein the tube has at least one open channel extending along a length thereof, and the hair grafts are slid through the tube by inserting a tool into the at least one open channel and biasing the hair grafts toward said first end of the tube.

3. The method of claim 2, wherein the tube has a plurality of channels, each channel containing a hair graft.

* * * * *